United States Patent
Magsood et al.

(10) Patent No.: US 11,373,552 B2
(45) Date of Patent: Jun. 28, 2022

(54) ANATOMICALLY ACCURATE BRAIN PHANTOMS AND METHODS FOR MAKING AND USING THE SAME

(71) Applicant: Virginia Commonwealth University, Richmond, VA (US)

(72) Inventors: Hamzah Magsood, Henrico, VA (US); Ciro H. Alcoba Serrate, Richmond, VA (US); Ahmed A. El-Gendy, Richmond, VA (US); Ravi L. Hadimani, Glen Allen, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 236 days.

(21) Appl. No.: 16/104,217

(22) Filed: Aug. 17, 2018

(65) Prior Publication Data
US 2019/0057623 A1    Feb. 21, 2019

Related U.S. Application Data

(60) Provisional application No. 62/546,810, filed on Aug. 17, 2017.

(51) Int. Cl.
| | |
|---|---|
| *G09B 23/28* | (2006.01) |
| *G09B 23/30* | (2006.01) |
| *A61N 2/00* | (2006.01) |
| *A61L 31/06* | (2006.01) |
| *A61L 31/02* | (2006.01) |
| *B29C 64/10* | (2017.01) |

(Continued)

(52) U.S. Cl.
CPC .......... *G09B 23/286* (2013.01); *A61L 31/024* (2013.01); *A61L 31/06* (2013.01); *A61N 2/006* (2013.01); *B29C 33/3842* (2013.01); *B29C 39/003* (2013.01); *B29C 64/10* (2017.08); *B33Y 80/00* (2014.12); *G01R 33/58* (2013.01); *G09B 23/30* (2013.01); *B29K 2083/00* (2013.01); *B29K 2105/167* (2013.01); *B29K 2507/04* (2013.01); *B29L 2031/40* (2013.01); *G01R 33/56341* (2013.01)

(58) Field of Classification Search
CPC .................. G09B 23/30; G09B 23/286; B29K 2105/167; B29C 33/00
See application file for complete search history.

(56) References Cited

U.S. PATENT DOCUMENTS

| | | | | |
|---|---|---|---|---|
| 4,010,554 A | * | 3/1977 | Compton | ................. G01N 1/06 434/297 |
| 6,336,812 B1 | * | 1/2002 | Cooper | ................ G09B 23/285 434/262 |

(Continued)

OTHER PUBLICATIONS

Serrate, "Development of Brain Phantom for Neuromodulation and Neuroimaging," abstract, available at http://absimage.aps.org/image/SES16/MWS_SES16-2016-000201.pdf, submission date Oct. 7, 2016 (Year: 2016).*

(Continued)

*Primary Examiner* — Matthew J Daniels
*Assistant Examiner* — Andrew D Graham
(74) *Attorney, Agent, or Firm* — W&C IP

(57) ABSTRACT

Anatomically accurate brain phantoms are disclosed which may be patient specific and used for experimentally testing neuromodulation and neuroimaging procedures.

14 Claims, 12 Drawing Sheets
(8 of 12 Drawing Sheet(s) Filed in Color)

(51) Int. Cl.
*B29C 39/00* (2006.01)
*G01R 33/58* (2006.01)
*B33Y 80/00* (2015.01)
*B29C 33/38* (2006.01)
B29L 31/40 (2006.01)
B29K 83/00 (2006.01)
B29K 105/16 (2006.01)
B29K 507/04 (2006.01)
G01R 33/563 (2006.01)

(56) References Cited

U.S. PATENT DOCUMENTS

| | | | | |
|---|---|---|---|---|
| 6,965,235 | B1* | 11/2005 | Guclu | G01R 33/58 |
| | | | | 324/318 |
| 9,994,812 | B2* | 6/2018 | Kim | C12N 5/0696 |
| 10,130,274 | B2* | 11/2018 | Voros | A61N 1/303 |
| 10,350,833 | B1* | 7/2019 | Zaneveld | B29C 67/0088 |
| 2003/0086535 | A1* | 5/2003 | Teppaz | A61B 6/583 |
| | | | | 378/207 |
| 2004/0175685 | A1* | 9/2004 | Sze | G09B 23/286 |
| | | | | 434/270 |
| 2004/0199069 | A1* | 10/2004 | Connelly | G01R 33/285 |
| | | | | 600/412 |
| 2006/0199159 | A1* | 9/2006 | Ghiron | G09B 23/30 |
| | | | | 434/270 |
| 2008/0265882 | A1* | 10/2008 | Wiggins | G01R 33/58 |
| | | | | 324/308 |
| 2009/0058417 | A1* | 3/2009 | Yanasak | G01R 33/58 |
| | | | | 324/307 |
| 2011/0181836 | A1* | 7/2011 | Rowe | G09B 23/30 |
| | | | | 351/205 |
| 2011/0250585 | A1* | 10/2011 | Ingber | C12M 25/02 |
| | | | | 435/5 |
| 2012/0015339 | A1* | 1/2012 | Hendrickson | G09B 23/303 |
| | | | | 434/268 |
| 2012/0045743 | A1* | 2/2012 | Okano | G09B 23/30 |
| | | | | 434/272 |
| 2012/0070814 | A1* | 3/2012 | Iida | G09B 23/286 |
| | | | | 434/270 |
| 2012/0237557 | A1* | 9/2012 | Lewitus | A61K 47/6925 |
| | | | | 424/400 |
| 2013/0085736 | A1* | 4/2013 | Reihsen | G09B 23/28 |
| | | | | 703/11 |
| 2014/0145562 | A1* | 5/2014 | Siores | B29C 71/0081 |
| | | | | 310/339 |
| 2014/0249612 | A1* | 9/2014 | Bonmassar | C09K 19/3809 |
| | | | | 607/116 |
| 2014/0272870 | A1* | 9/2014 | Eichhorn | G09B 23/30 |
| | | | | 434/267 |
| 2015/0044656 | A1* | 2/2015 | Eichhorn | A61B 5/11 |
| | | | | 434/267 |
| 2015/0050734 | A1* | 2/2015 | Liedtke | A61N 1/05 |
| | | | | 435/375 |
| 2015/0140539 | A1* | 5/2015 | Zamierowski | G09B 23/303 |
| | | | | 434/268 |
| 2015/0294599 | A1* | 10/2015 | Nitsche | G09B 23/286 |
| | | | | 434/262 |
| 2016/0027341 | A1* | 1/2016 | Kerins | B29C 39/10 |
| | | | | 434/270 |
| 2016/0089106 | A1* | 3/2016 | Kirby | A61N 5/10 |
| | | | | 378/207 |
| 2016/0155364 | A1* | 6/2016 | Piron | B29C 33/3835 |
| | | | | 434/270 |
| 2016/0297119 | A1* | 10/2016 | Richmond | B29C 33/306 |
| 2016/0370285 | A1* | 12/2016 | Jang | G01N 21/278 |
| 2017/0120065 | A1* | 5/2017 | Jiles | A61N 2/02 |
| 2017/0151733 | A1* | 6/2017 | Lewis | B29C 64/106 |
| 2018/0030409 | A1* | 2/2018 | Lewis | C12N 5/0697 |
| 2018/0047305 | A1* | 2/2018 | Lee | G01M 7/08 |
| 2018/0130381 | A1* | 5/2018 | Tian | A61B 6/032 |
| 2019/0057623 | A1* | 2/2019 | Magsood | G01R 33/58 |
| 2019/0367884 | A1* | 12/2019 | Satchi-Fainaro | C12M 29/10 |

OTHER PUBLICATIONS

Forte et al. A composite hydrogel for brain tissue phantoms. Materials and Design: 112 (2016) p. 227-238.

* cited by examiner

ANATOMICALLY ACCURATE BRAIN PHANTOMS AND METHODS FOR MAKING AND USING THE SAME

CROSS-REFERENCE TO RELATED APPLICATIONS

This application claims the benefit of U.S. Provisional Patent Application No. 62/546,810, filed Aug. 17, 2017, the complete contents of which are herein incorporated by reference.

STATEMENT REGARDING FEDERALLY SPONSORED RESEARCH OR DEVELOPMENT

This invention was made with government support under Grant Number 1726617 awarded by the National Science Foundation (NSF). The government has certain rights in the invention.

FIELD OF THE INVENTION

The invention generally relates to anatomically accurate brain phantoms and, more particularly, unique brain phantoms, methods of making brain phantoms, and methods of using brain phantoms. In some embodiments brain phantoms are tailored for transcranial magnetic stimulation (TMS) simulation or other non-invasive neuromodulation techniques such as transcranial direct current stimulation (tDCS) or invasive neuromodulation techniques such as deep brain stimulation (DBS) or combination of invasive and non-invasive neuromodulation techniques.

BACKGROUND

Transcranial Magnetic Stimulation (TMS) is a non-invasive technique used for treatment and diagnosis of many neurological conditions and diseases. However, the experimental measurement of induced electric fields in the brain tissues is not well established or understood due to non-availability of anatomically realistic head/brain phantoms. The lack of anatomically realistic brain phantoms has made the experimental verification of induced electric fields in the brain tissues an impediment to the development of new treatment protocols.

Transcranial magnetic stimulation (TMS) is a non-invasive treatment for neurological and psychiatric disorders, but the strength of the induced electric field decreases with distance from the TMS coil and the precise nature of induced electrical and magnetic fields may not be safely measured in living patients being treated with TMS. Deep brain effects of TMS are still unclear and not well-studied.

SUMMARY

An aspect of some embodiments is a 3-D anatomically realistic brain phantom developed using segmentation of MRIs, construction of volumetric brain models, 3-D printing, casting using composite polymer that mimic the brain conductivities, or a combination thereof. Exemplary phantoms may be used for the purpose of evaluation of neuromodulation techniques such as Transcranial Magnetic Stimulation (TMS) or other non-invasive neuromodulation techniques such as transcranial direct current stimulation (tDCS) or invasive neuromodulation techniques such as DBS or combination of invasive and non-invasive neuromodulation techniques. The phantoms may also be used in the evaluation of quality assurance and quality control (QA/QT) of neuroimaging modalities like magnetic resonance imaging (MRI).

An aspect of some embodiments is the enablement of the professional in the field of brain modulation and treatment to test and preform actual brain stimulations that are accurate and matches the clinical setting of the of the treatments of TMS, tDCS, DBS or combination of them. There are currently no brain heterogenous phantoms that can experimentally verify TMS and tDCS parameters. Embodiments herein comprise brain phantoms and experimental verification of TMS, tDCS, DBS or combination treatment parameters with such brain phantoms.

An exemplary method is capable of producing patient specific three dimensional anatomically realistic head and brain models from MRI data. It may be used to test the safety of neuroimaging and invasive and non-invasive neuromodulation procedures prior to them being performed on the actual patient.

Exemplary embodiments may involve a 3-D anatomically realistic brain phantom that mimics the electrical conduction and mechanical stiffness of the brain. An exemplary phantom is producible using MRI images, software for brain tissue segmentation and image reconstruction, a 3-D printer, and polymer with conductive fillers. Varied loading of fillers may be used to differentiate different types of tissue in the brain or in the head.

In some embodiments, brain tissues of phantoms are divided into cerebrospinal fluid (CSF), white matter (WM), grey matter (GM), ventricles (containing CSF), and cerebellum. In an exemplary phantom according to the present invention, shells are printed for each tissue layer/structure of the brain and head. After printing the shells are filled with a conductive material (e.g., polydimethyl-siloxane (PDMS) or silicon with nanoparticles) that is capable of mimicking the conductive properties of different brain tissues.

In contrast to commercially available concentric spherical phantoms, exemplary embodiments disclosed herein involve producing anatomically accurate phantoms quickly and economically through 3D printing. These phantoms can also be 3D printed for specific patients using their MRI data which can be valuable for complex brain stimulation procedures such as deep brain stimulation (DBS).

In some embodiments, diffusion tensor imaging (DTI) is used to construct 3D fiber tract models usable for either finite element analysis for TMS simulation as well as for integration with physical brain phantoms for real world experimentation (as opposed to a computer simulation). The induced electric field throughout a fiber tract can be assessed, and parts of the deep brain are identifiable as receiving stimulation when the outer cortex of the brain is stimulated.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
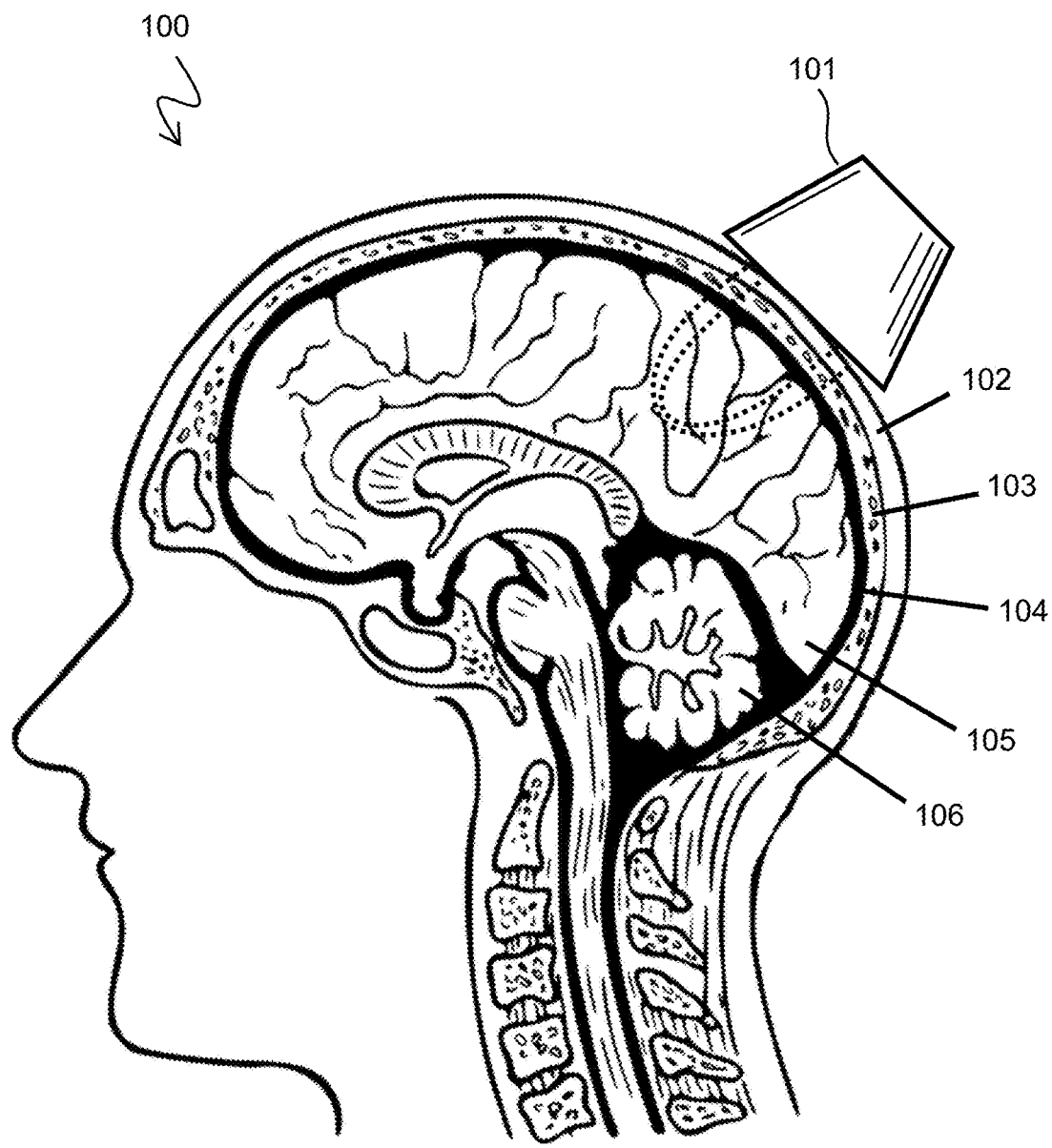
FIG. 1 shows anatomy within a human head undergoing transcranial magnetic stimulation (TMS).

FIG. 1 shows anatomy within a human head undergoing transcranial magnetic stimulation (TMS). The TMS device 101 is a non-invasive tool. It may be placed against the outside surface (e.g., skin) of the head 100 and produces one or more magnetic fields (shown with dotted lines in FIG. 1). The magnetic fields penetrate into the underlying brain tissue and act as a stimulus to a region of the brain. The treatment may be used to stimulate regions associated with mood disorders, for example. To reach the target tissue site, the stimulatory signal (e.g., the magnetic field) must traverse skin tissue 102, bone tissue (skull) 103, cerebrospinal fluid (104), and some amount of neural tissue (brain) 105. The stimulus may also reach the cerebellum 106 to some extent. In order to improve the effectiveness of TMS, it is desirable if not essential to understand how the parameters of the TMS device 101 affect different areas or parts of the patient's anatomy. Some exemplary embodiments meet this need by the provision of a 3-D anatomically realistic brain phantom ("phantom" for short) developed using 3-D printing.

For some exemplary phantoms according to the present invention, shells are 3D printed for each tissue layer of the brain. After printing, these shells are filled with a conductive material (e.g., silicon or PDMS with nanoparticles) that is configured to mimic the conductive properties of brain tissue. Different conductive material compositions may be used for different tissues (e.g., white matter vs. grey matter vs. CNF; brain matter vs. bone vs. skin).

Figure 2A:
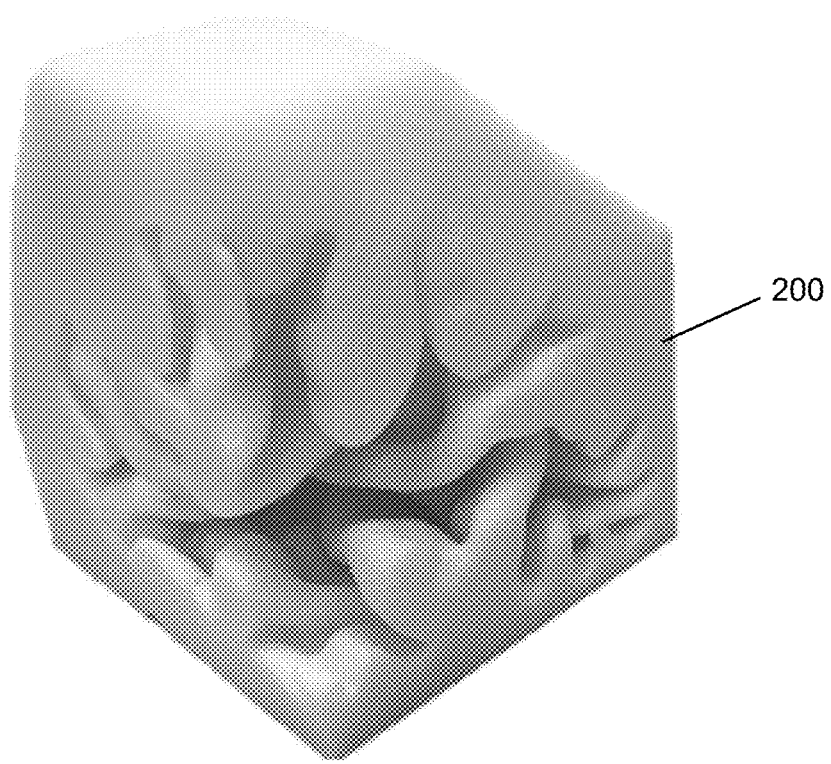
FIG. 2A shows a portion of a 3D-printed shell which defines the boundary geometry of a region of grey matter.
Figure 2B:
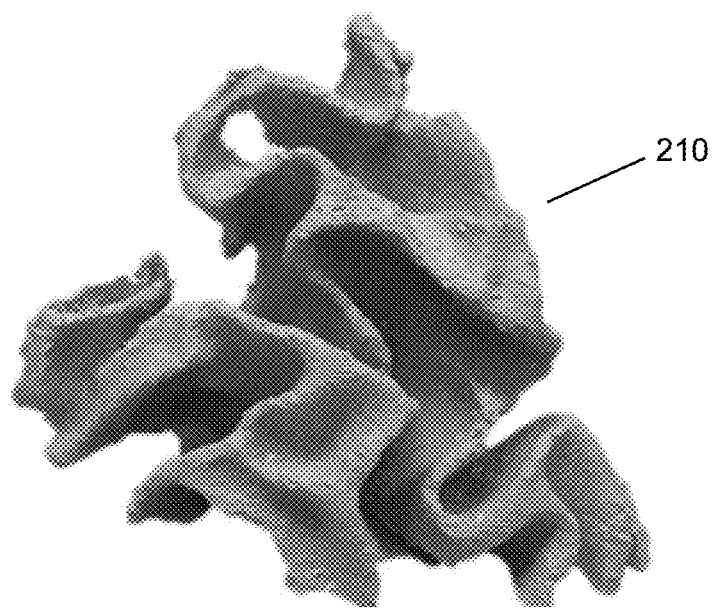
FIG. 2B shows cast material after it has been cured and the shell removed.

FIGS. 2A and 2B show samples from a prototype using 3D printing combined with casting. FIG. 2A shows a portion 200 of a 3D-printed shell which defines the boundary geometry of a region of grey matter. Suitable materials for shells are those which are 3D printable, shape resilient, and cable of being dissolved by subsequent chemical treatment. An exemplary material meeting these criteria may be a thermoplastic polymer such as Acrylonitrile butadiene styrene (ABS). The shell 200 may be used as mold for casting the conductive material which belongs in the phantom at the end of the manufacturing process. FIG. 2B shows cast material 210 after it has been cured and the shell 200 removed.

Figure 3A:
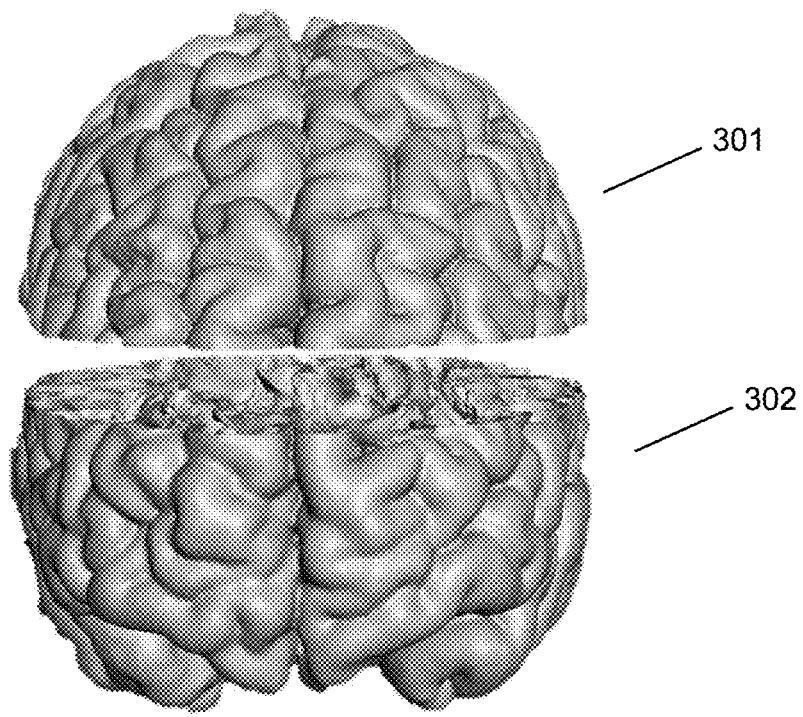
FIG. 3A shows two shells which together form a pair for casting grey matter.
Figure 3B:
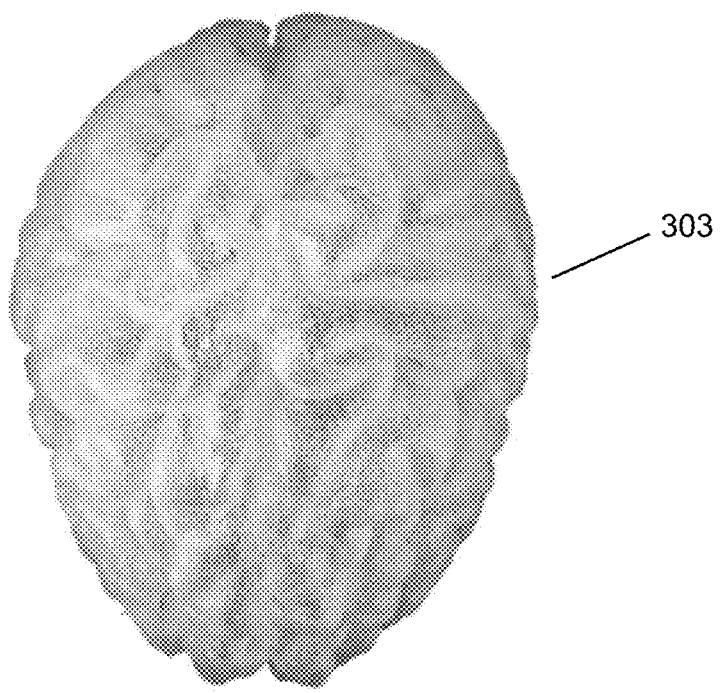
FIG. 3B shows the (unitary) grey matter casting produced from the shells of FIG. 3A.

FIG. 3A shows two shells 301 and 302 which together form a pair for casting grey matter. FIG. 3B shows the (unitary) grey matter casting 303 produced from the shells 301 and 302. Generally, casting of a brain phantom may be facilitated by making pairs of shells for respective parts of the brain, each pair having a top part (i.e., upper part) and a bottom part (i.e., lower part). This approach may be used for some elements of the brain phantom and not for others. For instance, using a pair of shells (one upper part and one lower part) may be especially well suited for casting grey matter, cerebrospinal fluid (CSF), bone, and skin. For parts such as the ventricles and cerebellum, a single shell may be used.

Figure 4A:
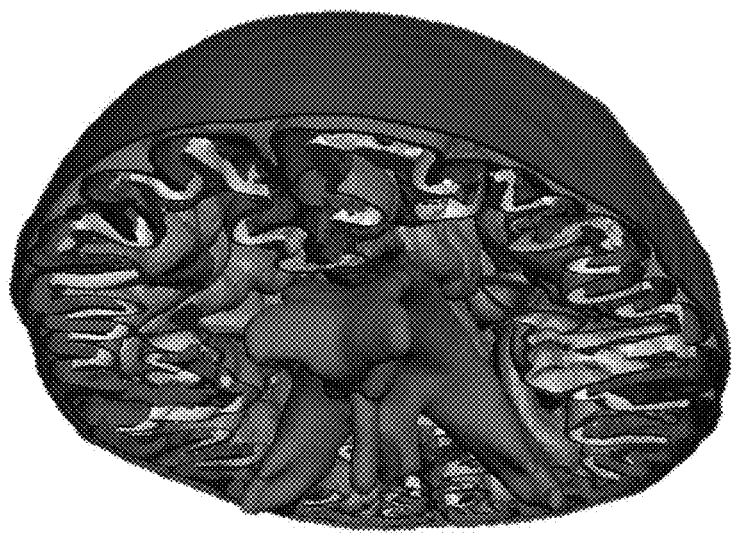
FIGS. 4A and 4B depict multiple shells in a software program (prior to 3D printing) arranged together in a manner consistent with human anatomy.
Figure 4B:
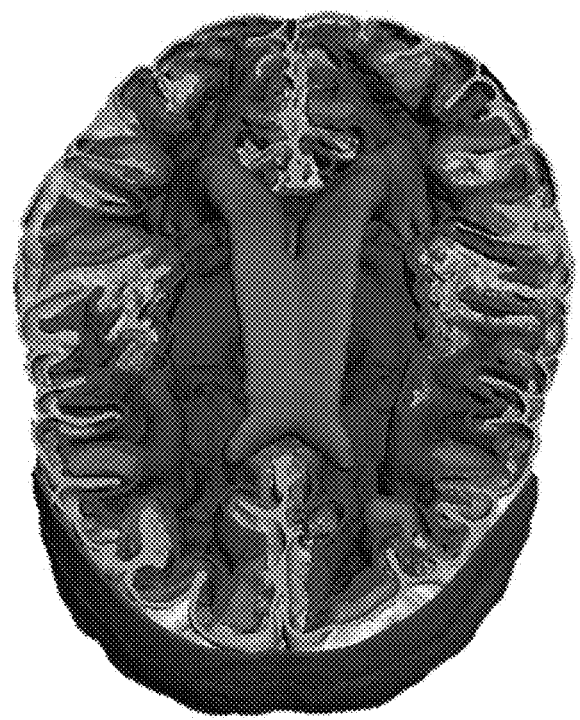

FIGS. 4A and 4B depict multiple shells arranged together in a manner consistent with human anatomy. The images were produced by the program, Meshmixer, the output of which may be sent to a 3D printer. As discussed above, shells for the skin, skull, and grey matter may be 3D printed in pairs comprising both upper and lower parts. The ventricles, however, may be cast using a single shell. In some instances, a shell (be it upper or lower) may technically consist of two shells, respectively referred to as an inner shell and outer shell. As will be discussed below, for example, grey matter may be cast using inner and outer upper shells as well as inner and outer lower shells.

Figure 5:
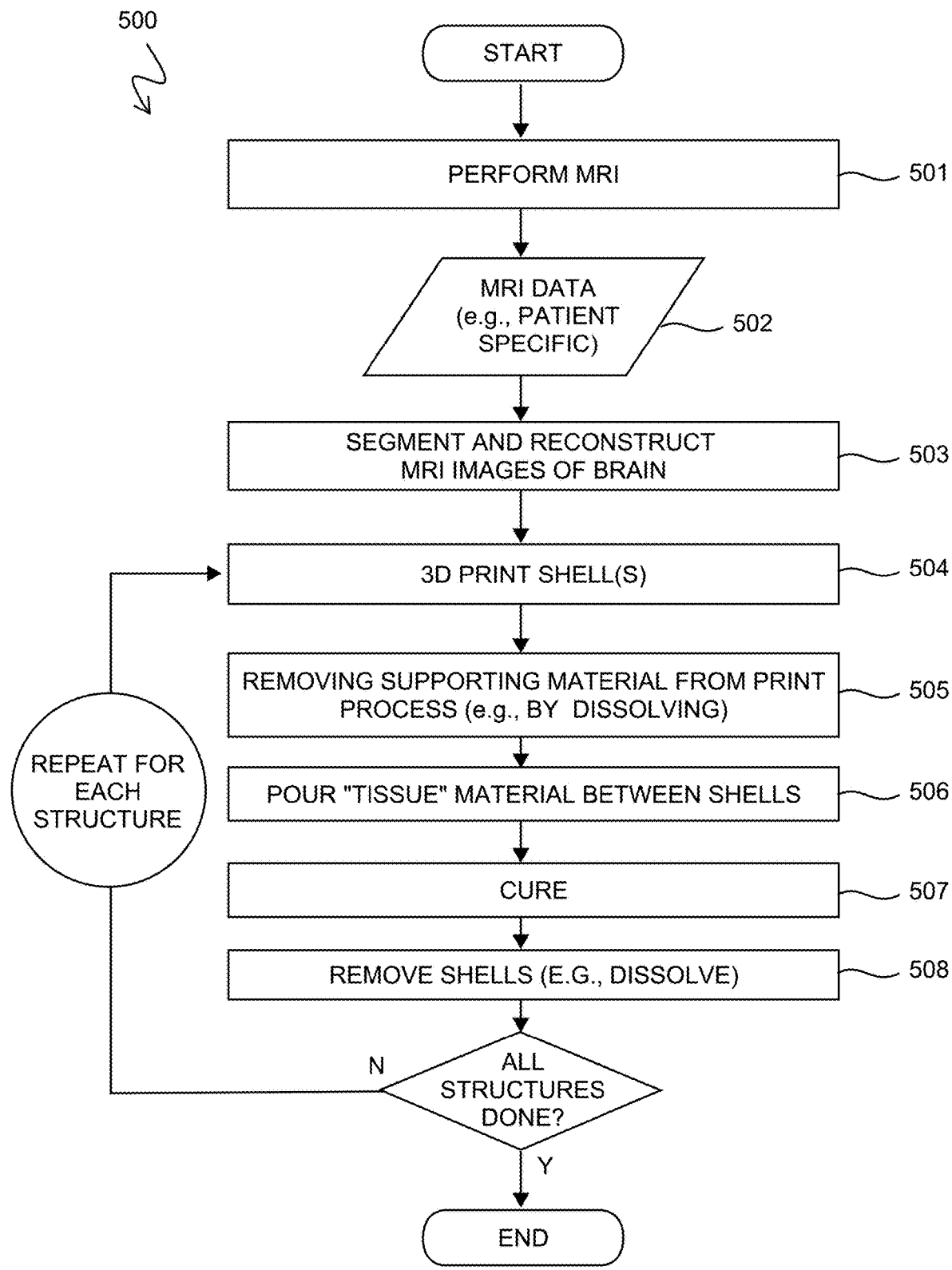
FIG. 5 is a process 500 for manufacturing a brain phantom according to combined manufacturing techniques of 3D-printing and casting.

FIG. 5 is a process 500 for manufacturing a brain phantom according to combined manufacturing techniques of 3D-printing and casting. A high level of anatomical correctness may be achieved by using MRI data from an actual human head and brain as the basis for what the phantom should mimic. Accordingly, at block 501 an MRI procedure is performed to generate MRI data 502. Because some of the manufacturing approaches described herein are especially cost effective, it may be that different phantoms are made for different respective patients. Patient specific MRI data may be used in each case for producing the phantom.

At block 503 the MRI brain images are segmented and reconstructed using computer program tools. At the time of this application MRI data may have .nii file extensions, for example, and require conversion for 3D modeling prior to supplying the data to a 3D printer. Software suitable for block 503 at the time includes FreeSurfer, FSL, and simNIBS. The output of such programs may be imported to another program (e.g., Meshmixer) to actually make the shells.

Blocks 503 to 508 walk through the production, use, and disposal of shells. In other words, these steps detail both mold making, casting, and mold removal. At block 503 shells are actually manufactured in a tangible form. 3D printing is an exemplary means for producing the shells in a cost effective manner. An exemplary material for the 3D printing process is an ABS (Acrylonitrile butadiene styrene) material. 3D printing may require the printing of supporting structures which do not actually have any anatomical analog. In such case these supporting structures may be removed at block 505 by, for example, chemically dissolving the parts (e.g., with acetone for ABS). Next the conductive "tissue" material is poured between shells (e.g., between and upper and lower shell pair, and/or between an inner and outer shell pair) at block 506, and permitted to cure at block 507. The curing process may involve time during which the chemical composition of the "tissue" material reacts and sets. The curing process may involve exposing the "tissue" material to some form of electromagnetic radiation that triggers curing or just keeping the material at environmental conditions for a finite duration of time.

After the conductive "tissue" material cures, the shells and the conductive material are placed in an appropriate chemical bath (e.g., Acetone) to dissolve all remaining shell material (e.g., ABS) at block 508, leaving only the cast "tissue" material for the phantom behind. The mold-making and casting of blocks 504 to 508 are repeated for subsequent parts. As will be discussed in greater detail below, for some tissue structures a prior casting may be used in place of one or more shells. As a result some tissue structures of the phantom are produced using two or more shells, some with only one shell, and some without any shells. Advantages of this approach are many. Fewer shells means less 3D printing which means lower costs of production. Using a prior casting of an existing part as the "mold" for the next part also means the two tissues will intimately share a boundary and reduce or avoid the possibility of gaps between phantom layers which could negatively affect the conductive behavior across the material-to-material boundary. At the conclusion of process 500 all shells have been removed and a multi-layered brain phantom remains and is ready for use.

Figure 6A:
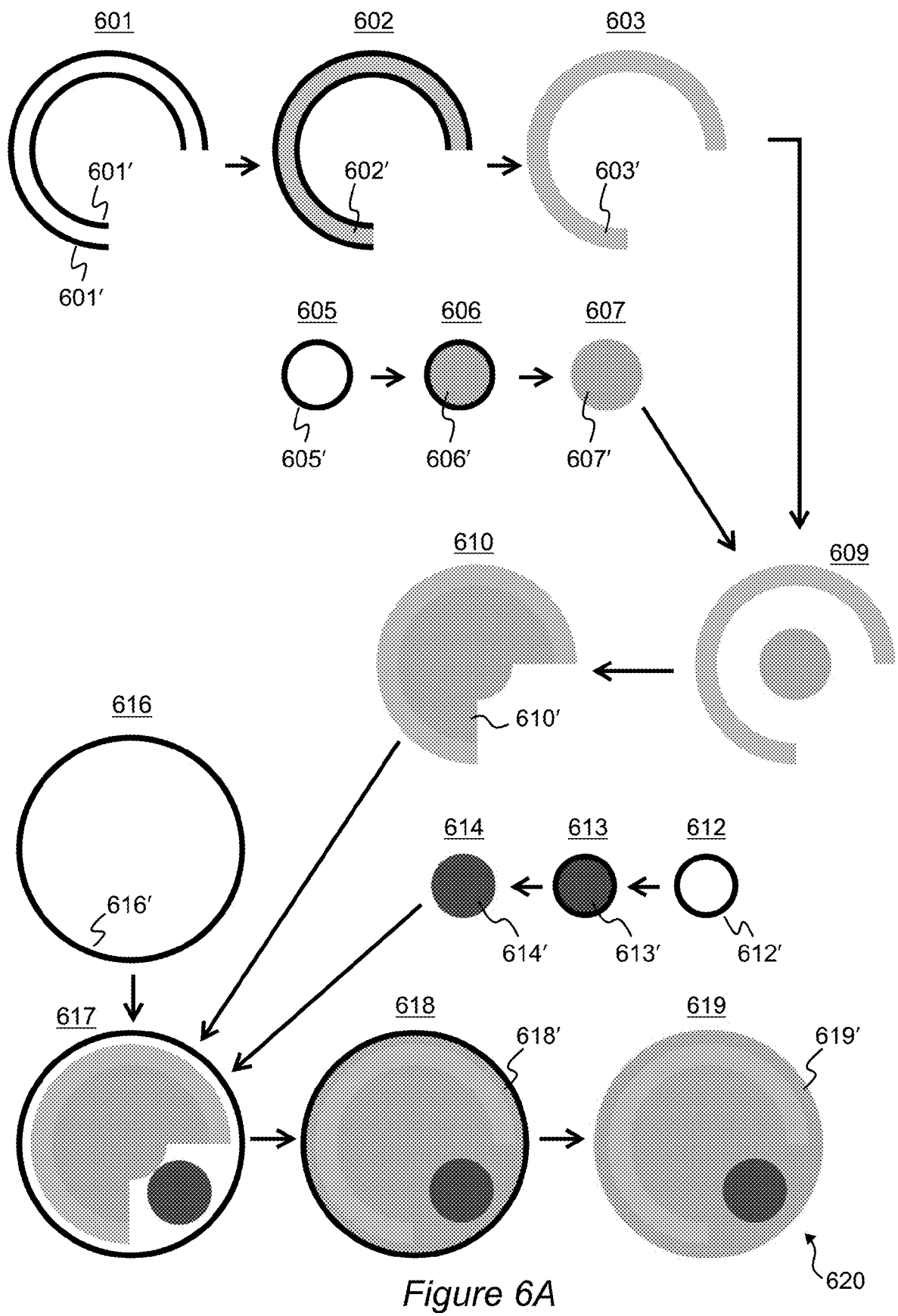
FIGS. 6A and 6B illustrate an exemplary process for manufacturing a brain phantom configured to mimic a brain or one or more structures thereof.
Figure 6B:
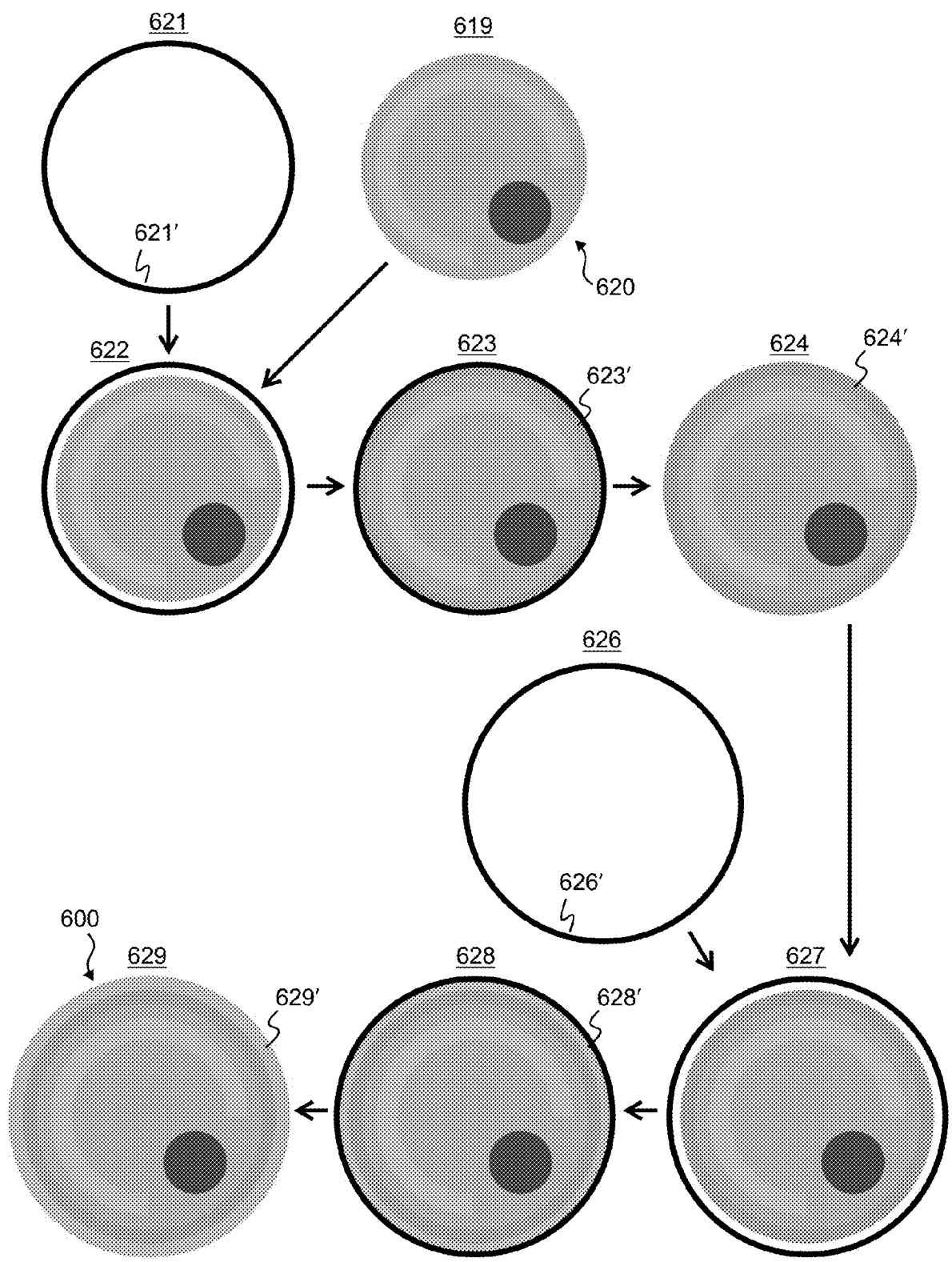

FIGS. 6A and 6B illustrate an exemplary process for manufacturing an anatomically accurate brain phantom 600 configured to mimic a brain or one or more structures thereof. Generally, the illustrated process corresponds with process 500 of FIG. 5, in particular block 504 and after. For ease of illustration, the dimensions and surface geometries of individual layers of material are oversimplified into basic geometric shapes (e.g., circles). In addition, the distinctions among upper vs. lower shells and inner vs. outer shells may be omitted to avoid overcomplicating the figures. It will be appreciated by ones of skill in the art that reference to "a shell" in the singular may be understood as indicative of multiple shells, for example a pair or two pairs of shells. Similarly, single shells may be used in some instances where a plurality is described. The details on shell pairing are already described above.

The end result of the process illustrated by FIGS. 6A and 6B is a complete brain phantom 600 containing one or more "tissue" structures, preferably at least six differentiated "tissues". These are grey matter, white matter, cerebrospinal fluid (CSF, including that which surrounds the brain and that which is contained in the ventricles), cerebellum, bone, and skin. Note that CSF may be referred to as a tissue or structure herein despite technically being a fluid in living organisms. Note also the ventricles may be referred to as a tissue or structure despite technically being cavities in living organisms. In the context of brain phantoms, both CSF and ventricles (which in living organisms are filled with CSF) may be simulated with solid or semisolid materials.

At stage 601, inner and outer shells 601' for grey matter (GM) are 3D printed and any supporting structures related to the printing process (and not anatomy) are removed. At stage 602 conductive material 602' is poured in between the inner and outer shells. The conductive material cures. At stage 603 the shells are removed. For example, the shells and conductive material are bathed in acetone (or other suitable dissolving agent) to dissolve the shell material, leaving only the cured grey matter material 603' remaining. The cured grey matter material is configured to be anatomically accurate with (e.g., mimic) grey matter found in naturally occurring grey matter of the brain.

At stage 605, a shell 605' is 3D printed for the ventricles and any supporting structures related to the printing process removed. At stage 606 conductive material 606' is poured inside the shell. The conductive material cures. At stage 607 the shell and conductive material are bathed in dissolving agent to dissolve the shell material, leaving only the cured ventricle material 607'. The cured ventricle material is configured to be anatomically accurate with (e.g., mimic) CSF ordinarily found in naturally occurring ventricles of the brain.

At stage 609, the cured and shell-less grey matter material from stage 603 and ventricle material from stage 607 are arranged together with anatomically correct three-dimensional spacing and orientation. The ventricle material is placed in the proper position inside the grey matter (GM) material. At stage 610 conductive material 610' simulating white matter (WM) is poured in the gaps between the ventricle material and GM and cured. Stage 610 differs notably from stages 602 and 606 in that no shells are necessary or indeed used according to some exemplary embodiments. Instead, the existing ventricle and GM castings serve as the mold for defining the boundaries of the WM, just as in real anatomy. The elimination of any shells to make the WM reduces both time and money costs involved in 3D printing and provides excellent interfaces among the grey matter, white matter, and ventricle material.

At stage 612 a shell 612' is 3D printed for the cerebellum and any supporting structures related to the printing process removed. At stage 613 conductive material 613' is poured inside the shell. The conductive material cures. At stage 614 the shell and conductive material are bathed in dissolving agent to dissolve the shell material, leaving only the cured cerebellum material 614'. The cured cerebellum material is configured to be anatomically accurate with (e.g., mimic) a cerebellum found in a naturally occurring brain.

At stage 616 a shell 616' is 3D printed for the cerebrospinal fluid (CSF) layer that envelopes the brain. At stage 617, the shell, the cerebellum, and the already assembled ventricle/WM/GM pieces are arranged together with anatomically correct three-dimensional spacing and orientation. One or more reference frames may be used to position the cerebellum in the assembly with the right location and orientation. For example, a 3D Cartesian table may be used to accurately assembly the brain regions. At stage 618 conductive material 618' which mimics CSF properties is poured into the spaces within the shell and cured. At stage 619 the shell is dissolved, leaving a fully cured and assembled unitary brain phantom 620 from the CSF layer and deeper. The cured CSF material 619' is configured to be anatomically accurate with (e.g., mimic) CSF ordinarily found in a naturally occurring brain. In some embodiments the brain phantom 620 produced at stage 619 may serve as an end product of the manufacturing process. The phantom 620 is suitable for use in simulations, tests, and experimentation relating to open surgery on the brain (e.g., where the skin and bone are removed).

FIG. 6B continues the manufacturing process for producing brain phantoms used or usable in connection with transcranial procedures. Two additional layers of material are still to be added: bone and skin. At stage 621 a shell 621' is 3D printed to define the outer boundary of the skull. At stage 622 the CSF-and-deeper brain phantom 620 of stage 619 is arranged within the shell. At stage 623 the remaining space within the shell is filled with conductive material 623' configured to mimic the skull bone tissue. The fluid is cured. At stage 624 the shell is removed. The cured bone material 624' is configured to be anatomically accurate with (e.g., mimic) skull bone ordinarily found in a naturally occurring head.

At stage 626 a shell 626' is 3D printed which defines the outer boundary of the skin surrounding the skull. At stage 627 the phantom from stage 624 is arranged within the shell 626'. At stage 628 the space between the shell and bone layer is filled with material 628' configured to mimic skin tissue and cured. At stage 629 the shell is removed. The cured skin material 629' is configured to be anatomically accurate with (e.g., mimic) skin ordinarily found on a naturally occurring head. The final result is a unitary brain phantom 600 which resembles the brain of the original MRI data and has distinguishable parts including skin, bone, CSF, cerebellum, grey matter, white matter, and ventricles (containing CSF).

In the preceding descriptions, removal of shells after material cast within the shell is cured has generally been described as performed via dissolving in a chemical bath. Alternative shell removal techniques may also be used in embodiments. For instance, shells may in some cases be broken and the resulting fragments removed (without any dissolving necessary).

Figure 7:
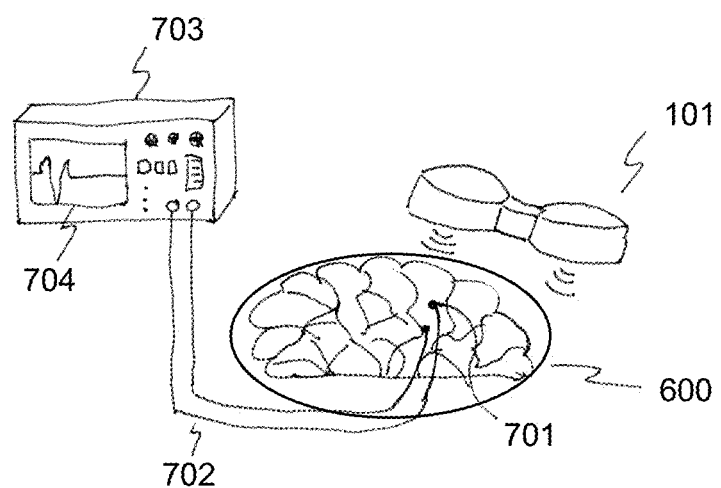
FIG. 7 is a diagram of an exemplary experimental setup in which transcranial magnetic stimulation (TMS) may be tested on a brain phantom.

FIG. 7 is a diagram of an exemplary experimental setup in which transcranial magnetic stimulation (TMS) may be tested on a brain phantom 600. Such a setup advantageously permits TMS trials on a phantom made to mimic the actual brain of a patient who is to be treated with TMS. A TMS device 101 is used or usable to subject to the phantom 600 to simulation, and the stimulatory signal may be measured by one or more electrodes 701 (e.g., microelectrodes) inserted or imbedded at different locations inside the phantom 600. Such electrodes 701 would not necessarily be implantable in the actual patient, at least not without an increased risk of harm to the patient. The phantom 600 which is configured to mimic the patient's brain serves as a ready substitute in which electrodes 701 can be inserted without any risk to the patient. The signals detected by the electrodes 701 may be transmitted, e.g. by wires 702, to a recording and/or display device 703 with an output (e.g., display 704) for study or processing. Parameters of the TMS device 101 may then be selected, adjusted and/or set based on the signals received from the electrodes 701.

An exemplary phantom is usable for the purpose of evaluation of the neuromodulation such as transcranial magnetic stimulation (TMS). It enables the professional in the field of the brain modulation and treatment to test and perform actual brain stimulations on the phantom that are accurate and match the clinical setting of the of TMS treatment. Prior to the instant invention, no brain phantoms existed to the knowledge of the inventor which were capable of experimentally verifying TMS parameters. An exemplary phantom is examinable under different TMS parameters and suitable for comparison with FEM modelling of induced electric field and magnetic fields in different tissues of the brain. Microelectrodes may be placed at different locations/ depths on the phantom to measure the current I and resistance Ω. Since the phantom exhibits same electrical properties of the brain, close readings to actual TMS procedures may be achieved.

Figure 8:
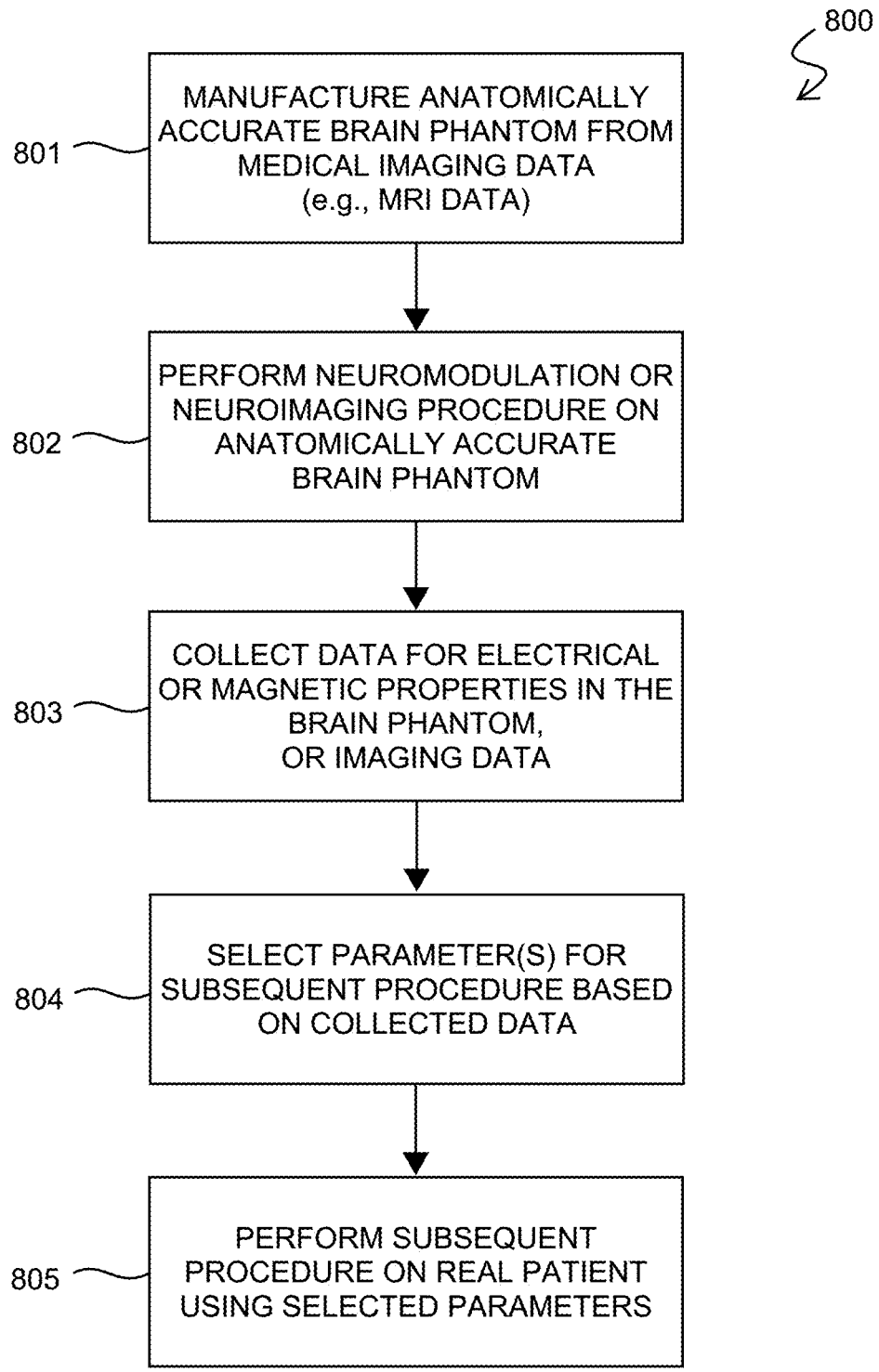
FIG. 8 is a flowchart of an exemplary method of performing a neuromodulation or neuroimaging procedure.

FIG. 8 presents an exemplary method 800 for performing a neuromodulation or neuroimaging procedure. The method 800 may be employed for providing personalized medicine. At block 801 an anatomically accurate brain phantom is manufactured. This process may be as described above. The process at block 801 may use patient-specific MRI data that is specific to the patient for which a future medical procedure is planned. At block 802, a neuromodulation or neuroimaging procedure is actually performed on the anatomically accurate brain phantom. The procedure may be invasive, non-invasive, or some combination thereof. Multiple procedures (e.g., a series of procedures) may be performed on the same brain phantom. Neuromodulation procedures may include one or more of transcranial magnetic stimulation (TMS), transcranial direct current stimulation (tDCS), or deep brain stimulation (DBS). Neuroimaging procedures may include magnetic resonance imaging, for example. Other procedures may also or alternatively be performed.

At block 803, data is collected as the medical procedure is performed. If the procedure is a neuromodulation procedure, electrical or magnetic properties in the brain phantom may be obtained during the neuromodulation procedure (e.g., see FIG. 7 and accompany description). If the procedure is a neuroimaging procedure, image data may be obtained during the neuroimaging procedure (e.g., MRI data). From the collected data, medical software and/or practitioners (e.g., doctors) may select parameters for a subsequent procedure at block 804, where the parameters are customized for the patient whose MRI data was used to construct the brain phantom. The parameters may be, for example, one or more of power settings, intensity settings, wavelength or frequency settings, duration settings, interval settings, and impulse settings, among others. Indeed, any setting which may be adjusted on existing or future medical devices like TMS devices or MRI machines may be calibrated or customized for a particular patient using the method 800.

In connection with the selection process in block 804, the data collected at block 803 may be compared to reference data, and the selection may be based on the comparison. For example, particular stimulatory conditions may be desired at a particular location within a patient's brain. The desired stimulatory conditions may be saved as reference data. TMS may then be performed using initial settings and the stimulatory response measured. The TMS device settings can be adjusted until the desired stimulatory conditions within the brain phantom are reached. The final TMS settings may then be used for actually treating the patient.

At block 805 the subsequent neuromodulation or neuroimaging procedure is actually performed on the patient using the selected parameters.

Exemplary methods like method 800 may be useful for personalized medicine for any patient, human or animal. Method 800 is especially advantageous for patients with unique or abnormal conditions which set them apart from the anatomy typical of most patients. For example, some patients may already have a brain implant such as a DBS device. In such a case any effects of the presence of the existing implant on neuroimaging or neuromodulation may be unknown or uncertain. Method 800 permits a safe and reliable means for assessing how such a procedure may go using an anatomically accurate phantom mimicking the patient's brain and containing a copy of the patient's implant to select the parameters of performing the procedure. The procedure may then be performed on the actual patient with a greater degree of certainty and safety.

In the above descriptions for manufacturing brain phantoms, the materials used for the phantom layers are generally described as conductive materials. Addressing the materials directly, an exemplary conductive material is a silicon or silicone based compound (a compound containing silicon, Si) or PDMS with one or more of graphite, multi walled or single walled carbon nanotubes (MWCNT/SWCNT), and silver nanoparticles and nanowires that is capable of mimicking the electrical conductive properties of different brain tissues based on the respective amounts of these constituents. Some embodiments use specific ratios of all three additives in the silicon base. The silicon base may be, for example, silicon polymer polydimethylsiloxane PDM. The conductivity of layers of an exemplary phantom may be in the range between 0.2-3.0 Sm$^{-1}$. For the skin layer the conductivity range may be lower, e.g., as low as 0.1 Sm$^{-1}$. In some other embodiments the layers may each be in the range of 0.2-1.8 Sm$^{-1}$. In a particular example, the electrical conductivity of different brain tissue that was matched in a phantom was as follows: ventricles & CSF=1.77 Sm$^{-1}$, GM=0.23 Sm$^{-1}$, WM=0.24 Sm$^{-1}$, and cerebellum=0.65 Sm$^{-1}$.

An "anatomically accurate" brain phantom mimics the brain of a living organism, e.g. a mammalian brain (e.g., a human brain). Anatomically accurate may mean the three dimensional geometry (e.g., sizes, relative sizes, dimensions, relative dimensions, locations or positions, relative locations or positions, etc.) of the phantom matches or substantially matches the three dimensional geometry of a real brain (e.g., an actual mammalian brain). Anatomically accurate may mean one or more electrical properties (e.g., electrical conductivity) of the brain phantom match or substantially match one or more electrical properties of a real brain (e.g., an actual mammalian brain). Anatomically accurate may mean one or more material properties (e.g., mass density, viscosity, etc.) of the brain phantom match or substantially match one or more material properties of a real brain (e.g., an actual mammalian brain). A brain phantom may match or substantially match a real brain if at least one layer/structure of the brain phantom matches or substantially matches the corresponding real brain structure. A brain phantom may match or substantially match a real brain only if all the layers/structures of the brain phantom match or substantially match the real brain. Table 1 below presents exemplary but non-limiting material properties which may be used in a computer simulation or physical brain phantom which is anatomically accurate.

TABLE 1

Material properties for simulation or physical brain phantoms

| Structure | Mass Density (kg/m$^3$) | Electrical Conductivity (S/m) | Relative Permittivity |
|---|---|---|---|
| Skin | 1109 | 0.17 | 1 |
| Skull | 1908 | 0.32 | 1 |
| CSF/Ventricles | 1007 | 1.7765 | 1 |
| Grey Matter | 1044.5 | 0.239149 | 1 |
| White Matter | 1041 | 0.26507 | 1 |
| Cerebellum | 1045 | 0.659667 | 1 |

The published literature on the conductivity of healthy adult brain's white matter, grey matter, CSF, skull and skin varies significantly. However, the most trusted values of conductivities for grey and white matter fall in the range of 0.1 to 0.5 S/m. Therefore an anatomically accurate brain phantom may be produced with the conductivities of the grey matter and white matter in the range of 0.1 to 0.5 Sm$^{-1}$. Different conductivities may be used for different structures/layers/regions of the brain phantom. To achieve different conductivities, different composite polymers may be prepared and used. For example, exemplary brain phantoms or structures/layers thereof may comprise a composite polymer of a silicon-based compound (e.g., PDMS) and carbon nanotubes (in particular multi-walled carbon nanotubes, MWCNTs) with the conductivity/resistivity varied among the structures/layers by variable wt % of the MWCNTs. Table 2 presents the relationship between resistivity and composition of MWCNTs in PDMS.

TABLE 2

Relationship between resistivity and composition of MWCNTs

| wt % of CNT in PDMS | Resistivity (ohm/cm) |
|---|---|
| 10.5 | 1000 |
| 11.5 | 500 |
| 12.5 | 300 |
| 15.3 | 35 |

Resistivity of 300-400 ohms/cm corresponds to 0.3-0.5 S/m (an exemplary target value range for WM and GM). An exemplary composition used for Example 1 below is 11.5 wt % of MWCNTs composition for GM and WM.

Layers or structures of exemplary brain phantoms may have electrical conductivities varied with respect to one another by varying one or more of the materials or compositional ratios with respect to the other layers/structures. For example, different layers or structures may be configured to have different electrical conductivities based on nanotubes of different lengths in one layer versus another layer (e.g., shorter in one layer versus longer in another layer). Different layers or structures may be configured to have different electrical conductivities based on different materials for the nanotubes in one layer versus another layer (e.g., carbon versus silver). Different layers or structures may be configured to have different electrical conductivities based on different types of nanotubes in one layer versus another layer (e.g., single walled versus multi walled nanotubes). In some exemplary embodiments which use a combination of PDMS with MWCNTs, the wt % of CNT in PDMS may be between 10.5 and 15.3 with a resistivity between 1000 and 35 ohm/cm. In some exemplary embodiments which use a combination of PDMS with MWCNTs, the wt % of CNT in PDMS may be 10.5 to 12.5 with a resistivity between 1000 and 300 ohm/cm. In some exemplary embodiments which use a combination of PDMS with MWCNTs, the wt % of CNT in PDMS may be about 11.5 (e.g., 11.5±0.5) with a resistivity of or about 500 ohm/cm. Other exemplary specifications may be used in other embodiments.

In some embodiments, brain phantoms may comprise integrated fiber tracts. An important feature in the brain that is normally (and disadvantageously) ignored by researchers while calculating induced electric fields is fiber tracts due to their anatomical complexities and small dimensions. The fiber tracts are part of the white matter with high conductivity and impart anisotropy to the white matter. In some embodiments, fiber tracts may be made an integral part of a brain phantom.

Figure 11:
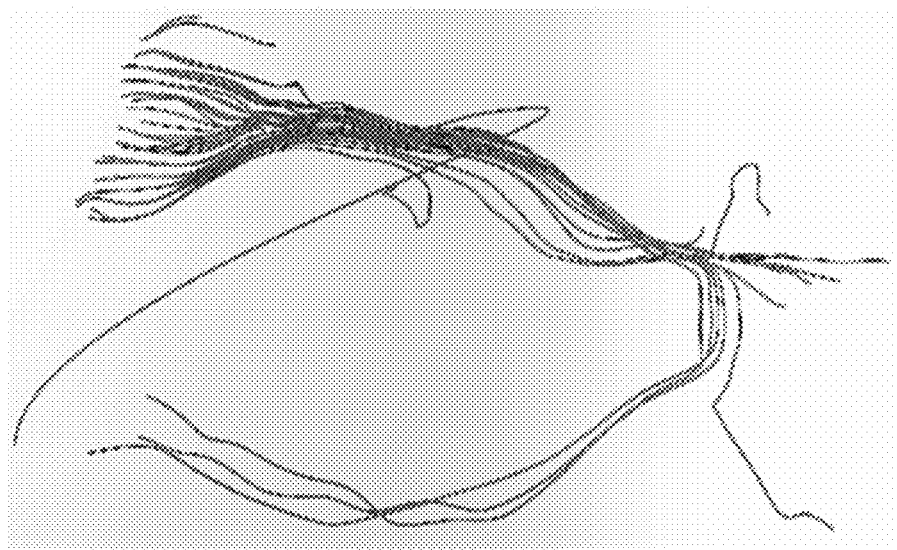
FIG. 11 shows modeled fiber tracts constructed with CAD software.
Figure 10:
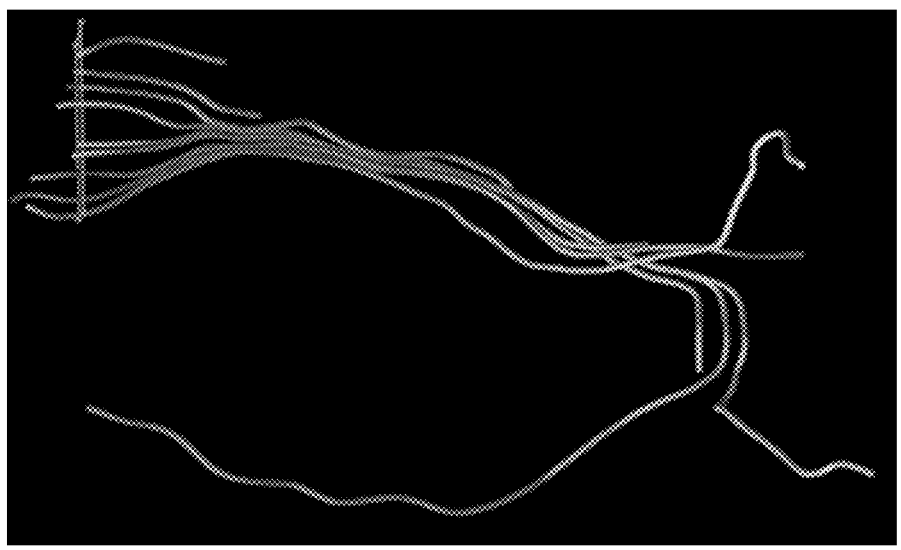
FIG. 10 shows modeled fiber tracts as constructed within the graphical toolbox ExploreDTI.

Following is an example approach for integrating one or more fiber tracts into a brain phantom. High resolution diffusion tensor imaging (DTI) data is collected. Then fiber tracts are extracted from the DTI data using, for example, a graphical toolbox ExploreDTI. Then fiber tracts are constructed using whole brain tractography. Tracts are drawn from a seed region of interest (ROI) such as M1 with parameters such as the following: a seed fractional anisotropy threshold of 0.2, minimum fiber length of 50 mm, and angle threshold of 30 degrees. FIG. 10 shows the resulting fiber tracts originating from the ROI of M1 within an ExploreDTI interface. Next coordinates of tracts are imported into a CAD modeling software such as SolidWorks to form curved paths, and then each path is extruded to a solid, 3D object. FIG. 11 shows the 3D fiber objects within a SolidWorks interface.

Figure 12:
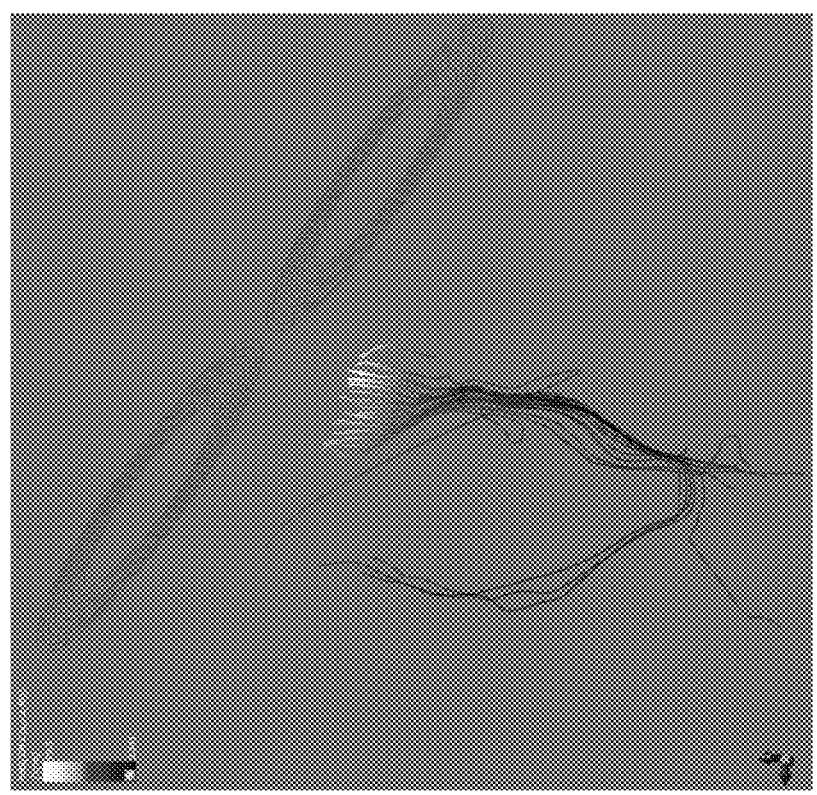
FIG. 12 shows modeled fibers in a simulation of TMS using simulation program, Sim4Life.

The 3D fiber (CAD) models can be exported (e.g., as .STL files) for finite element analysis in a simulation program such as Sim4Life. FIG. 12 shows fibers being stimulated by a Figure-Eight TMS coil.

Figure 13:
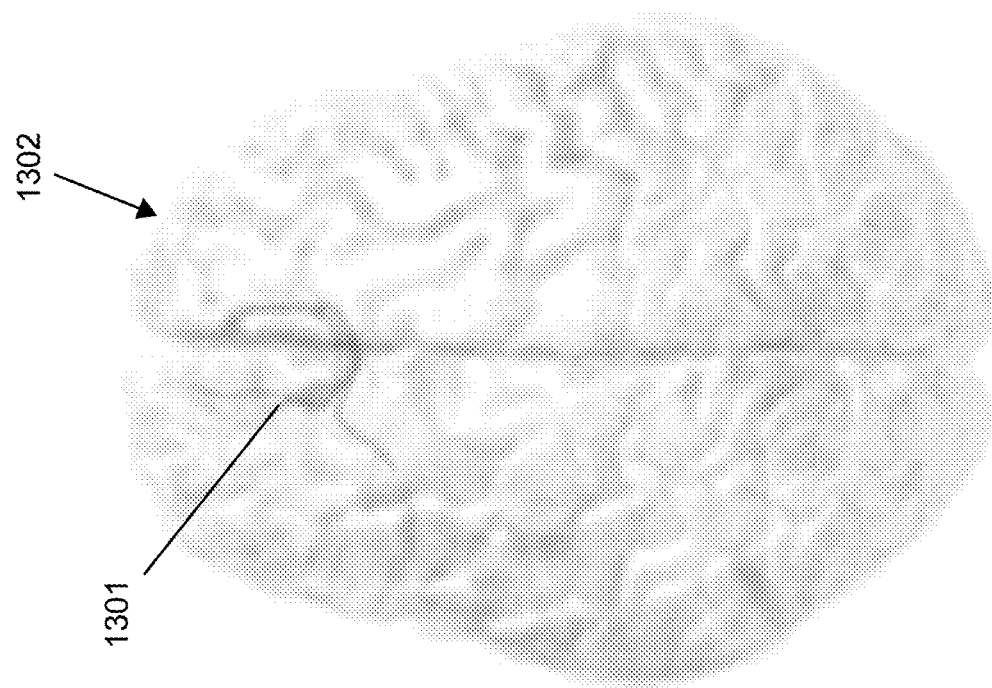
FIG. 13 shows 3D fibers integrated within a brain phantom.

The 3D fiber (CAD) models may also be integrated directly into a brain phantom. FIG. 13 shows the 3D fibers 1301 integrated within the brain phantom 1302. The fiber models may be embedded into a 3D head/brain models to experimentally calculate induced electric field during TMS in different regions of the brain. The brain phantoms may be used in testing of various coil configurations to tune the electric field strengths in the targeted regions of the brain.

Integration of fiber tracts to a brain phantom may involve different or modified manufacturing processes than described above. Integration of fiber tracts in brain phantom needs conductive polymers that have less viscosity. Preparation of soft polymers with high conductivity is a complex process with many variables. The volume fraction/loading factor of conductive materials in a polymer composite increases the viscosity of the polymer and makes it difficult to conform to complex structures, such as fiber tracts, for white and grey matter of the brain. The conductivity of the polymer composite is sensitive to the length of carbon nanotubes or the nanowires used. In some embodiments, carbon nanotubes longer than 50 μm are used to make the hardness of the polymer composite a suitable level. Phantoms may be fabricated using the PDMS/CNT composite in a 3D Bioplotter® which is a multi-nozzle, 3D printer of UV curable soft materials. With a 3D printer like the 3D Bioplotter®, the use of shells and casting may be avoided (although the cost of production may be substantially increased). A 3D printer like the Bioplotter® is used or usable to print complex shapes to simultaneously fabricate all the regions of the phantom (e.g., the parts described above), including the fiber tracts. Electrical and magnetic fields may be induced in the resulting brain phantom as previously described in connection with FIG. 7.

Where computer software is discussed herein, it should be understood that such software may be embodied in computer readable instructions which may be provided to one or more processors of a general purpose computer, special purpose computer, or other programmable data processing apparatus to produce a machine, such that the instructions, which execute via the processor of the computer or other programmable data processing apparatus, create means for implementing the functions/acts specified in the description above, in one of the flowcharts, and/or in one or more block diagram blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagrams. Embodiments herein may comprise one or more computers, one or more processors, one or more computer readable storage media, and/or appropriate input/output devices therefore, as well as additional supporting hardware as necessary.

Unless the context indicates otherwise, block diagrams and flowcharts are exemplary and may involve fewer or greater number of blocks and/or a different order of items or steps. In some embodiments elements or steps may be concurrent, combined, or otherwise organized differently than is depicted or described.

EXAMPLES

Example 1. Experimental Verification of Transcranial Magnetic Stimulation Using Anatomically Accurate Brain Phantom A phantom was produced by 3-D printed shells for each tissue layer of the brain. Brain tissues were divided into cerebrospinal fluid (CSF), white matter (WM), grey matter (GM), ventricles, and cerebellum. These layers were made into shells defining their geometric spatial boundaries and 3D printed. The shells were then filled with a conductive material (silicon polymer polydimethylsiloxane PDM with electrically conductive filler multi walled carbon nanotubes MWCNT) to impart electrical conduction to the brain phantom. Then, the shells were broken or dissolved to finally produce the brain phantom. The electrical conductivity of the brain phantom tissue was is in the range of 0.4-1.0 $Sm^{-1}$. The phantom was then examined under different TMS parameters and compared with FEM modelling of induced electric and magnetic fields in the brain.

Figure 9:
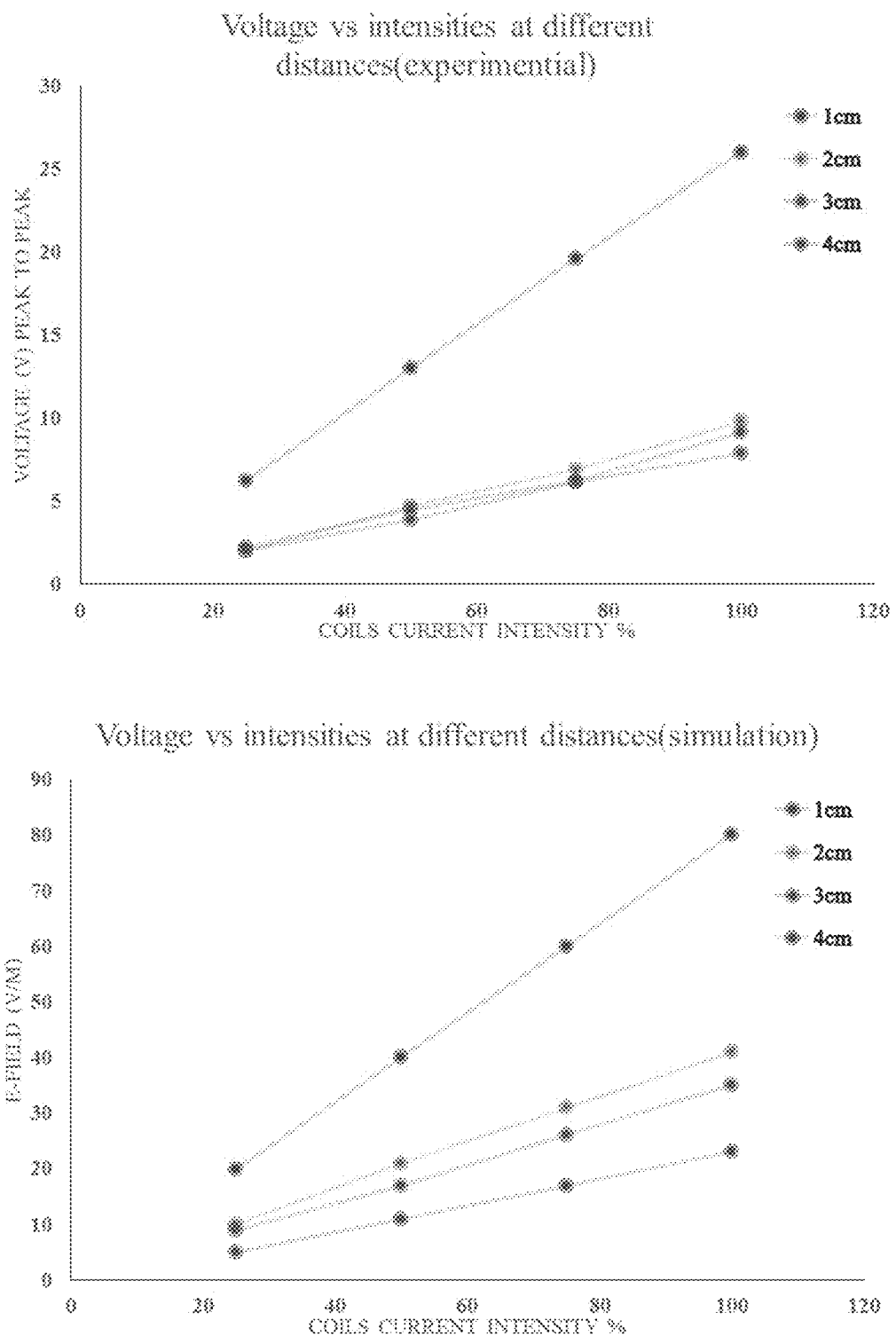
FIG. 9 is experimental and simulation data for TMS.

TMS device coils were positioned on the brain phantom and an oscilloscope probe was placed just underneath the surface of the phantom in order to measure the voltage (phantom probe). Another probe was placed at the same distance (from the coils) as the first probe but outside the phantom so as to measure the voltage induced on the probe just from the TMS coils (reference probe). Then, the magnetic field from the coils was applied. The process was repeated for four distances total: 1, 2, 3, and 4 cm. At each distance measurements were repeated at four different power intensities: 25, 50, 75, and 100%. The brain phantom and experimental set up corresponds with FIG. 7. The same settings were replicated with an FEM simulation (i.e., the virtual coils in the software were places at four distances 1, 2, 3, and 4 cm form the surface of the brain model and with four intensities 25, 50, 75, and 100% at each distance). The voltage readings for both the phantom experimental and computer simulation cases are shown in FIG. 9. Voltage readings of the experimental work shown in the upper graph of FIG. 9 represent the difference between the voltages induced on the phantom probe and the reference probe. The results indicate that there is a noticeable induced electric field in the phantom due to the applied magnetic field from the TMS coils.

Next comparing both graphs, experimental (FIG. 9, top) and simulation (FIG. 9, bottom), it can be seen that there is an overall similar behavior. The voltage and e-field readings are linearly dependent with intensity in both graphs. Also, the induced voltage decreases almost exponentially with the distance.

Example 2. 3D Modeling of Diffusion Tensor Imaging Tractography Data for Finite Element Analysis DTI data was collected from a single subject, healthy 30 year old male patient on a GE 3T HDx scanner with 60 directions. This data was visualized in the graphical toolbox ExploreDTI. Fiber tracts were constructed using whole brain tractography with the following parameters: seed fractional anisotropy threshold of 0.2, minimum fiber length of 50 mm, angle threshold of 30 degrees, and a step size of 1. Tracts were calculated and drawn from a seed ROI drawn on the z-plane around the M1 region. The coordinates of each individual tract were imported into SolidWorks as a curve which could then be extruded to a solid, 3D object with a diameter of 0.25 mm. These 3D fiber models were exported as STL files for finite element analysis to simulate TMS alongside 3D brain tissue models.

FIG. 10 shows the tracts drawn from the M1 region. Thirty-four tracts were found with an average length of 87.09 mm. Note that while the data shows 34 distinct tracts, all 34 are not apparent in FIG. 10. The paths of some of these fibers appear to follow the corticospinal tract. Finite element analysis of the fiber tracts alongside a brain tissue model and a FIG. 9 TMS coil produced high currents at tract points by the cortex which gradually decreased towards the deep brain.

The ability to 3D model fiber tracts allows for a more comprehensive study of the deep brain effects of cortical stimulation. Tractography constructs the pathways of fiber tracts, allowing for visualization of connecting regions of the brain. Finite element analysis calculates the magnitude of the electric field at any point on the tract. Knowing this can help determine if and where TMS can be used to stimulate the deep parts of the brain by stimulating the cortical regions and improve therapies for disorders affecting the deep brain.

While exemplary embodiments of the present invention have been disclosed herein, one skilled in the art will recognize that various changes and modifications may be made without departing from the scope of the invention as defined by the following claims.

We claim:

1. A method of producing an anatomically accurate brain phantom, comprising
   forming an anatomically accurate inner shell and an outer shell that mimic an inner surface and an outer surface of a brain structure;
   pouring a conductive material comprising silicon and carbon nanotubes in between the inner shell and the outer shell;
   curing the conductive material; and
   removing the inner shell and the outer shell to provide a brain phantom of said brain structure, wherein silicon and carbon nanotubes are present throughout the brain structure as to produce a relatively lower electrical conductivity at a skin portion of the brain structure and
   wherein the brain structure is shaped to mimic at least one of white matter (WM), grey matter (GM), ventricles, and cerebellum.

2. The method of claim 1, further comprising forming a plurality of additional layers which are part of the brain phantom by
   pouring conductive material comprising silicon and carbon nanotubes (CNTs) between either
      at least one additional anatomically accurate shell and an existing layer of the brain phantom, or
      two existing layers of the brain phantom;
   curing the conductive material; and
   removing the at least one additional shell if an additional shell was used in the pouring step.

3. The method of claim 2, wherein the plurality of additional layers are configured to mimic brain structures including cerebrospinal fluid (CSF), white matter (WM), grey matter (GM), ventricles, and cerebellum.

4. The method of claim 2, further comprising configuring the plurality of layers to have different conductivities with respect to one another by varying the wt % of CNTs from one layer to the next.

5. The method of claim 1, wherein the forming step comprises 3D printing the anatomically accurate inner and outer shells.

6. The method of claim 1, wherein the forming step uses medical imaging data of a mammalian brain to determine three dimensional geometry of the anatomically accurate inner and outer shells.

7. The method of claim 6, further comprising segmenting and reconstructing MRI brain images with a computer program to produce segmented brain tissues corresponding to the separate shells to be formed.

8. A method of producing an anatomically accurate brain phantom, comprising
   forming an anatomically accurate inner shell and an outer shell that mimic an inner surface and an outer surface of a brain structure;
   pouring a conductive material comprising silicon and carbon nanotubes in between the inner shell and the outer shell;
   curing the conductive material; and
   removing the inner shell and the outer shell to provide a brain phantom of said brain structure, wherein silicon and carbon nanotubes are present throughout the brain structure as to produce a relatively higher electrical conductivity at a cerebrospinal fluid (CSF) portion of the brain structure and
   wherein the brain structure is shaped to mimic at least one of white matter (WM), grey matter (GM), ventricles, and cerebellum.

9. The method of claim 8, further comprising forming a plurality of additional layers which are part of the brain phantom by
   pouring conductive material comprising silicon and carbon nanotubes (CNTs) between either
      at least one additional anatomically accurate shell and an existing layer of the brain phantom, or
      two existing layers of the brain phantom;
   curing the conductive material; and
   removing the at least one additional shell if an additional shell was used in the pouring step.

10. The method of claim 9, wherein the plurality of additional layers are configured to mimic brain structures including white matter (WM), grey matter (GM), ventricles, and cerebellum.

11. The method of claim 9, further comprising configuring the plurality of layers to have different conductivities with respect to one another by varying the wt % of CNTs from one layer to the next.

12. The method of claim 8, wherein the forming step comprises 3D printing the anatomically accurate inner and outer shells.

13. The method of claim 8, wherein the forming step uses medical imaging data of a mammalian brain to determine three dimensional geometry of the anatomically accurate inner and outer shells.

14. The method of claim 13, further comprising segmenting and reconstructing MRI brain images with a computer program to produce segmented brain tissues corresponding to the separate shells to be formed.

* * * * *